United States Patent [19]

Elliott et al.

[11] Patent Number: 5,736,564
[45] Date of Patent: Apr. 7, 1998

[54] ENDOTHELIN RECEPTOR ANTAGONISTS

[75] Inventors: John Duncan Elliott, Wayne; Robert Gene Franz, Plymouth Meeting; M. Amparo Lago, Audubon; Aiming Gao, Chester Springs, all of Pa.

[73] Assignee: SmithKline Beecham Corporation, Philadelphia, Pa.

[21] Appl. No.: 464,761

[22] PCT Filed: Jun. 6, 1995

[86] PCT No.: PCT/US95/07193

§ 371 Date: Dec. 12, 1996

§ 102(e) Date: Dec. 12, 1996

[87] PCT Pub. No.: WO95/35107

PCT Pub. Date: Dec. 28, 1995

Related U.S. Application Data

[63] Continuation-in-part of Ser. No. 262,801, Jun. 20, 1994.

[51] Int. Cl.$^6$ .......... A61K 31/40; C07D 209/08
[52] U.S. Cl. .......... 514/414; 514/416; 548/466; 548/472
[58] Field of Search .......... 514/414, 416; 548/466, 472

[56]     References Cited

FOREIGN PATENT DOCUMENTS

| | | |
|---|---|---|
| 0227986 | 7/1987 | European Pat. Off. . |
| 1229653 | 4/1971 | United Kingdom . |

*Primary Examiner*—Joseph McKane
*Attorney, Agent, or Firm*—Linda E. Hall; Stephen A. Venetianer; Edward T. Lentz

[57]     ABSTRACT

The present invention relates to dihydroisoindole compounds, pharmaceutical compositions containing these compounds, and their use as endothelin receptor antagonists.

6 Claims, No Drawings

ENDOTHELIN RECEPTOR ANTAGONISTS

This patent is a continuation-in-part of U.S. Ser. No. 262,801 filed Jun. 20, 1994.

This application is a 371 of PCT/US95/07193 filed Jun. 6, 1995.

FIELD OF THE INVENTION

The present invention relates to novel dihydroisoindole derivatives, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99:597–601, 1989 and Clozel and Clozel, Circ. Res., 65:1193–1200, 1989) coronary vasospasm (Fukuda et al., Eur. J. Pharm. 165:301–304, 1989 and Lüscher, Circ. 83:701, 1991) heart failure, proliferation of vascular smooth muscle cells, (Takagi, Biochem & Biophys. Res. Commun.; 168:537–543, 1990, Bobek et al., Am. J. Physiol. 258:408-C415, 1990) and atherosclerosis, (Nakaki et al., Biochem. & Biophys. Res. Commun. 158:880–881, 1989, and Lerman et al., New Eng. J. of Med. 325:997–1001, 1991). Increased levels of endothelin have been shown after coronary balloon angioplasty (Kadel et al., No. 2491 Circ. 82:627, 1990).

Further, endothelin has been found to be a potent constrictor of isolated mammalian airway tissue including human bronchus (Uchida et al., Eur J. of Pharm. 154:227–228 1988, LaGente, Clin. Exp. Allergy 20:343–348, 1990; and Springall et al., Lancet, 337:697–701, 1991). Endothelin may play a role in the pathogenesis of interstitial pulmonary fibrosis and associated pulmonary hypertension, Giard et al., Third International Conference on Endothelin, 1993, p. 34 and ARDS (Adult Respiratory Distress Syndrome), Sanai et al., Supra, p. 112.

Endothelin has been associated with the induction of hemorrhagic and necrotic damage in the gastric mucosa (Whittle et al., Br. J. Pharm. 95:1011–1013, 1988); Raynaud's phenomenon, Cinniniello et al., Lancet 337:114–115, 1991); Crohn's Disease and ulcerative colitis, Munch et al., Lancet, Vol. 339, p. 381; Migraine (Edmeads, Headache, Feb. 1991 p 127); Sepsis (Weitzberg et al., Circ. Shock 33:222–227, 1991; Pittet et al., Ann. Surg. 213:262–264, 1991), Cyclosporin-induced renal failure or hypertension (Eur. J. Pharmacol., 180:191–192, 1990, Kidney Int, 37:1487–1491, 1990) and endotoxin shock and other endotoxin induced diseases (Biochem, Biophys. Res. Commun., 161:1220–1227, 1989, Acta Physiol. Scand. 137:317–318, 1989) and inflammatory skin diseases. (Clin Res. 41:451 and 484, 1993) and macular degeneration.

Endothelin has also been implicated in preclampsia of pregnancy. Clark et al., Am. J. Obstet. Gynecol. March 1992, p. 962–968; Kamor et al., N. Eng. J. of Med., Nov. 22, 1990, p. 1486–1487: Dekker et al., Eur J. Ob. and Gyn. and Rep. Bio. 40 (1991) 215–220; Schiff et al., Am. J. Obstet. Gynecol. Feb. 1992, p. 624–628; diabetes mellitus, Takahashi et al., Diabetologia (1990) 33:306–310; and acute vascular rejection following kidney transplant, Watschinger et al., Transplantation Vol. 52, No. 4, pp. 743–746.

Endothelin stimulates both bone resorption and anabolism and may have a role in the coupling of bone remodeling. Tatrai et al. Endocrinology, Vol. 131, p. 603–607.

Endothelin has been reported to stimulate the transport of sperm in the uterine cavity. Casey et al., J. Clin. Endo and Metabolism, Vol. 74, No. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man, Lau et al., Asia Pacific J. of Pharm., 1991, 6:287–292 and Tejada et al., J. Amer. Physio. Soc. 1991, H1078–H1085. Endothelin also mediates a potent contraction of human prostatic smooth muscle, Langenstroer et al., J. Urology, Vol. 149, p. 495–499.

Thus, endothelin receptor antagonists would offer a unique approach toward the pharmacotherapy of hypertension, pulmonary, hypertension, renal failure, ischemia induced renal failure, sepsis-endotoxin induced renal failure, prophylaxis and/or treatment of radio-contrast induced renal failure, acute and chronic cyclosporin induced renal failure, cerebrovascular disease, myocardial ischemia, angina, heart failure, asthma, atherosclerosis, macular degeneration, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, preclampsia of pregnancy, bone remodeling, kidney transplant, male contraceptives, infertility and priaprism and benign prostatic hypertrophy.

SUMMARY OF THE INVENTION

This invention comprises dihydroisoindole derivatives represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, stroke, cerebrovascular vasospasm, myocardial ischemia, angina, heart failure and atherosclerosis, and as an adjunct in angioplasty for prevention of restenosis and for benign prostatic hypertrophy.

This invention further constitutes a method for antagonizing endothelin receptors in an animal, including humans, which comprises administering to an animal in need thereof an effective amount of a compound of Formula (I).

DETAILED DESCRIPTION OF THE INVENTION

The compounds of this invention are represented by structural Formula (I)

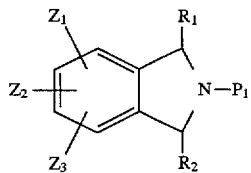

wherein:

$R_1$ is $-X(CH_2)_nAr$ or $-X(CH_2)_nR_8$ or $R_2$ is hydrogen, Ar or $C_{1-4}$alkyl;

$P_1$ is tetrazole, $SO_2NR_7R_{11}$, $CONR_7SO_2R_{11}$, or $(CH_2)_sR_8$;

$R_3$ and $R_5$ are independently hydrogen, $R_{11}$, OH, $C_{1-8}$alkoxy, $S(O)_qR_{11}$, $N(R_6)_2$, Br, F, I, Cl, $CF_3$, $NHCOR_6$, $R_{11}CO_2R_7$, $-X-R_9-Y$, or $-X(CH_2)_nR_8$ wherein each methylene group within $-X(CH_2)_nR_8$ may be unsubstituted or substituted by one or two $-(CH_2)_nAr$ groups;

$R_4$ is hydrogen, $R_{11}$, OH, $C_{1-5}$alkoxy, $S(O)_qR_{11}$, $N(R_6)_2$, $-X(R_{11})$, Br, F, I, Cl or $NHCOR_6$ wherein the $C_{1-5}$alkoxy may be unsubstituted or substituted by OH, methoxy or halogen;

$R_6$ is independently hydrogen or $C_{1-4}$alkyl;

$R_7$ is independently hydrogen, $C_{1-10}$alkyl, $C_{2-10}$alkenyl or $C_{2-8}$ alkynyl, all of which may be unsubstituted or substituted by one or more OH, $N(R_6)_2$, $CO_2R_{12}$, halogen or $XC_{1-5}$alkyl; or $R_7$ is $(CH_2)_nAr$;

$R_8$ is hydrogen, $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $-CO_2(CH_2)_mC(O)N(R_6)_2$, $C(R_{11})_2N(R_7)_2$, $C(O)N(R_6)_2$ or tetrazole;

$R_9$ is $(CH_2)_n$, $C_{1-10}$alkylene, $C_{2-10}$alkenylene or phenylenyl, all of which may be unsubstituted or substituted by one or more OH, $N(R_6)_2$, COOH, halogen, or $R_9$ may be $>C=O$ or $XC_{1-5}$alkyl;

$R_{11}$ is hydrogen, Ar, $C_{1-8}$alkylene, $C_{2-8}$alkenylene, $C_{2-8}$-alkynylene, all of which may be unsubstituted or substituted by one or more OH, $CH_2OH$, $N(R_6)_2$ or halogen;

$R_{12}$ is hydrogen, $C_{1-6}$alkyl, $C_{2-6}$alkenyl or $C_{2-7}$alkynyl;

X is $(CH_2)_n$, O or $NR_6$;

Y is $CH_3$ or $X(CH_2)_nAr$;

Ar is:

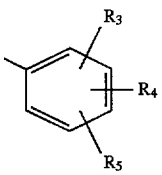 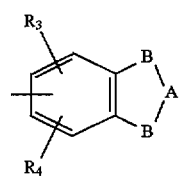

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstittited or substituted by one or more $R_3$ or $R_4$ groups;

A is C=O, or $[C(R_6)_2]_m$;

B is $-CH_2-$ or $-O-$;

$Z_1$ and $Z_2$ are independently hydrogen, $C_{1-8}$alkyl, $C_{2-8}$alkenyl, $C_{2-8}$alkynyl, OH, $C_{1-8}$alkoxy, $S(O)_qC_{1-8}$alkyl, $N(R_6)_2$, Br, F, I, Cl, $NHCOR_6$, $-X-R_9-Y$, $-X(CH_2)_nR_8$, phenyl, benzyl or $C_{3-6}$cycloalkyl wherein the $C_{1-8}$alkyl, $C_{2-8}$alkenyl or $C_{2-8}$alkynyl may be optionally substituted by COOH, OH, $CO(CH_2)_nCH_3$, $CO(CH_2)_nCH_2N(R_6)_2$, or halogen; or $Z_1$ and $Z_2$ together may be $-O-A-O-$ on contiguous carbons;

$Z_3$ is $Z_1$ or $-X-R_9-Y$;

q is zero, one or two;

n is an integer from 0 to six;

s is an integer from one to six;

m is 1, 2 or 3; and the dotted line indicates the optional presence of a double bond; provided $P_1$ is not $(CH_2)_sNH_2$; or a pharmaceutically acceptable salt thereof.

Also included in the invention are pharmaceutically acceptable salt complexes.

All alkyl, alkenyl, alkynyl and alkoxy groups may be straight or branched. The term "halogen" is used to mean iodo, fluoro, chloro or bromo. Alkyl groups may be substituted by one or more halogens up to perhalogenation.

The compounds of the present invention may contain one or more asymmetric carbon atoms and may exist in racemic and optically active form. All of these compounds and diastereoisomers are contemplated to be within the scope of the present invention.

The present invention provides compounds of formula (I) above,

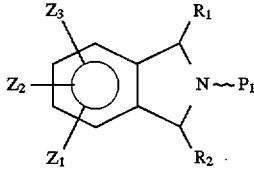

which can be prepared by reacting a suitably substituted orthobromobenzoic acid such as (2)

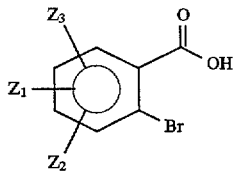

with two equivalents of n-Butyllithium in a solvent such as THF under argon at −78° C. followed by the addition of an acid chloride of formula (3)

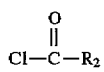   (3)

wherein $Z_1$, $Z_2$ and $Z_3$ are as defined in formula I, in a suitable solvent such as THF to provide a compound of formula (4)

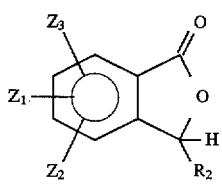   (5)

Treatment of compound (4) with a suitable reducing agent such as Zn in acetic acid provides a phenyl substituted phthalide of formula (5)

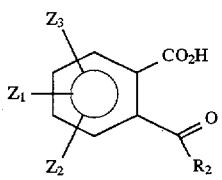   (4)

Treatment of (5) with an organomagesium compound of formula (6)

$R_1MgBr$   (6)

wherein $R_1$ is as defined in formula I, in a suitable solvent such as ether at reflux provides, after acid treatment, compounds of formula (7)

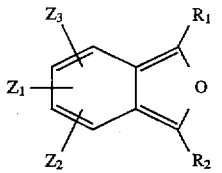   (7)

Oxidation of (7) under appropriate conditions such as with Jones reagent provides compounds of formula (8)

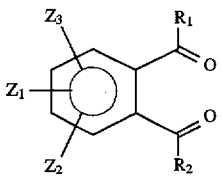   (8)

Isoindoles of formula (10) can be obtained by treatment of (8), with a primary amine of formula (9)

$H_2NQ$   (9)

wherein Q is hydrogen or $(CH_2)_sR_8$, in a suitable solvent such as ethanol at reflux; in the presence of sodium borohydride in ethanol.

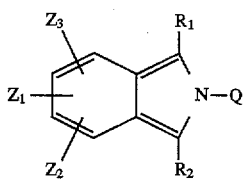   (10)

Reduction of an isoindole of formula (10) under the appropriate conditions such as Zn(Cu) in hot acetic acid or with hydrogen gas under pressure in the presence of a suitable catalyst such as 10% palladium on charcoal affords compounds of formula (11).

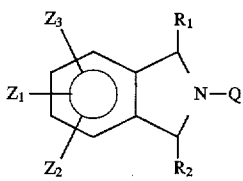   (11)

Compounds of formula (11) may be convened to those of formula (I) by acylation or alkylation of Q to $P_1$ as appropriate.

With appropriate manipulation and protection of any chemical functionalities, synthesis of the remaining compounds of the Formula (I) is accomplished by methods analogous to those above.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1a–1d) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or nonaqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) Membrane Preparation (Rat cerebellum or kidney cortex)

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000 x g for 10 minutes at 4° C. The supernatant was removed and centrifuged at 40,000 xg for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 micrograms of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteric artery bed. The homogenate was strained through cheesecloth and centrifuged at 2,000 xg for 10 min. at 4° C. The supernatant was removed and centrifuged at 40,000 xg for 30 min. at 4° C. The resulting pellet was resuspended as explained above for cerebellum and kidney cortex. Approximately 10 micrograms of membrane protein was used for each tube in binding experiments.

B) CHO Cell Membrane Preparation

CHO cells stably transfected with human $ET_A$ and $ET_B$ receptors were grown in 245 mm x 245 mm tissue culture plates in Dulbecco's modified Eagle's medium (DMEM) supplemented with 10% fetal bovine serum (FBS). The confluent cells were washed with DPBS (Dulbecco's phosphate buffered saline) containing protease inhibitor cockatil (5 mM EDTA, 0.5 mM PMSF, 5 ug/ml leupeptin, and 0.1 U/ml aprotinin) and scraped in the same buffer. After centrifugation at 800 xg, the cells were lysed by freezing in liquid nitrogen and thawing on ice followed by homogenization (30 times using glass dounce homogenizer) in lysis buffer containing 20 mM Tris HCl, pH 7.5 and the protease inhibitor cocktail. After an initital centrifugation at 800 xg for 10 min to remove unbroken cells and nuclei, the supernatants were centrifuged at 40,000 xg for 15 min and the pellet was resuspended in 50 mM Tris HCl, pH 7.5 and 10 mM $MgCl_2$ and stored in small aliquots at −70° C. after freezing in liquid $N_2$. Protein was determined using BCA method and bovine serum albumin as the standard.

C) [$^{125}$I]ET-1 Binding Protocol

[$^{125}$I]ET-1 binding to membranes from rat cerebellum (2–5 mg protein/assay tube) or kidney cortex (3–8 micrograms protein/assay tube) or CHO cell membranes (containing 4–6 and 1–2 micrograms of membrane protein for $ET_A$ and $ET_B$ receptors, respectively) were measured after 60 minutes incubation at 30° C. in 50 mM Tris HCl, 10 mM $MgCl_2$, 0.05% BSA, pH 7.5 buffer in a total volume of 100 microliters. Membrane protein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM $MgCl_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. $IC_{50}$'s for the compounds of this invention range from 0.01 nm to 50 uM.

II. In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; $KH_2PO_4$, 1.2; $MgSO_4$, 1.2; $CaCl_2$, 2.5; $NaHCO_3$, 25.0; and dextrose, 11.0. Tissue bath solutions are maintained at 37° C. and aerated continuously with 95% $O_2$/5% $CO_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean ±S.E.M. Dissociation constants ($K_b$) of competitive antagonists were determined by the standard method of Arunlakshana and Schild. The potency range for compounds of this invention range from 0.1 nM to 50 mm.

The following examples are illustrative and are not limiting of the compounds of this invention.

EXAMPLE 1

Preparation of (1RS,3RS)-[3-[(2-Carboxymethoxy-4-methoxy)phenyl]-1-(3,4-methylenedioxyphenyl)-5-(prop-1-yloxy) (1H,3H-dihydro-isoindol-2-yl)] acetic acid, trifluoroacetate salt.

a) Benzyl 3-(Prop-1-yloxy)benzoyl acetate

To a solution of benzyl alcohol (0.197 ml, 1.91 mmol), 4-dimethylaminopyridine (0.077 g, 0.64 mmol) in dry toluene (5 ml) under argon was added methyl 3-(prop-1-yloxy) benzoyl acetate (0.300 g, 1.27 mmol) in toluene (0.5 ml). The reaction was allowed to stirred at reflux for 24 h. On cooling the mixture was then quenched with saturated ammonium chloride and partitioned with ethyl acetate. The combined organic extracts was washed successively with: water, brine and dried ($MgSO_4$). After removing the solvent under reduced pressure, flash chromatography of the residue (silica gel, 3:7 ethyl acetate:hexane) afforded the title compound as a yellow oil (0.320 g, 80%).

b) Benzyl 3-(3,4-methylenedioxyphenyl)-2-[3-prop-1-yloxy)-benzoyl]propenoate

To a solution of 3,4-(methylenedioxy)benzaldehyde (4.81 g, 32.1 mmol), benzyl 3-(Prop-1-yloxy)benzoyl acetate (10.0 g, 32.1 mmol) in benzene (50 ml) was added piperidine (0.31 ml, 3.21 mmol) followed by acetic acid (10 drops). The reaction was allowed to stir at reflux equipped with a dean stark apparatus for 2 h. Upon removal of the solvent a yellow oil was obtained. Recrystallization from ethyl acetate/hexane afforded the title compound as an off white solid (9.8 g, 69%).

c) Benzyl-(1RS,2SR)-(3,4-methylenedioxyphenyl)-5-prop-1-yloxy-3-oxo-indane-2-carboxylate A solution of benzyl 3-(3,4-methylenedioxyphenyl)-2-[3-prop-1-yloxy)-benzoyl]propenoate (9.3 g, 20.9 mmol) in trifloroacetic acid (40 ml) was stirred at room temperature for 1.5 h. The solvent was removed and the resulting residue was dissolved in ethyl acetate washed successively with: water, 5% sodium bicarbonate and brine. The organic extract was dried ($MgSO_4$) and removal of the solvent under reduced pressure gave the title compound as a yellow oil (9.8 g, quantitative).

d) 1-(3,4-Methylenedioxyphenyl)-5-prop-1-yloxy-3-oxo-indane

To a solution of benzyl-(1RS,2SR)-(3,4-methylenedioxyphenyl)-5-prop-1-yloxy-3-oxo-indane-2-carboxylate (8.2 g, 18.4 mmol) in warm acetic acid (130 ml), was added under argon 10% Pd/C (4.1 g) followed by 1,4-cyclohexadiene (17.4 ml, 185 mmol). The reaction was exothermic and gas evolution was observed. The reaction was allowed to stir under argon at room temperature for 2 h. The mixture was filtered through a pad of celite and concentrated in vacuo. Flash chromatography of the residue (silica gel, 3:7 ethyl acetate:hexane) afforded the title compound as a pinkish solid (5.08 g, 93%).

e) 3-(3,4-Methylenedioxyphenyl)-6-prop-1-yloxy inden-1-one

A solution of 1-(3,4-methylenedioxyphenyl)-5-prop-1-yloxy-3-oxo-indane (2.7 g, 9.06 mmol), 2,3-dichloro-5,6-dicyano-1,4-benzoquinone (2.45 g, 10.87 mmol) in 1,4-dioxane (80 ml) was stirred at reflux for 2 h. The solvent was removed under reduced pressure and the resulting residue was dissolved in methylene chloride and filtered. The filtrate was concentrated and flash chromatography (silica gel, 3:7 ethyl acetate:hexane) afforded the title compound as a red solid (1.48 g, 55%).

f) (1RS)-1-[(2-Benzyloxy-4-methoxy)phenyl]-1-hydroxy-3-(3,4-methylenedioxyphenyl)-6-prop-1-yloxy-1H-indene To a solution of 3-(3,4-methylenedioxyphenyl)-6-prop-1-yloxy inden-1-one (2.2 g, 7.4 mmol) in THF (50 ml) at 0° C. under argon, was added dropwise a freshly prepared solution of 2-benzyloxy-4-methoxyphenyl magnesium bromide (7.07 g, 22.3 mmol) in a 1:1 mixture of THF:$Et_2O$ (30 ml, total). The reaction was stirred at 0° C. for 20 minutes. The mixture was then quenched with 1N HCl and extracted with ethyl acetate. The organic extract was then washed with water, brine, and dried ($MgSO_4$). After removing the solvent under reduced pressure, flash chromatography of the residue (silica gel, 3:7 ethyl acetate:hexane) afforded the title compound as off white crystals (1.77 g, 46%).

g) 1-(2-Benzyloxy-4-methoxybenzoyl)-2-(3,4-methylenedioxybenzoyl)-5-prop-1-yloxybenzene To a solution of (1RS)-1-[(2-Benzyloxy-4-methoxy)phenyl]-1-hydroxy-3-(3,4-methylenedioxyphenyl)-6-prop-1-yloxy-1H-indene (0.100 g, 0.19 mmol) in a mixture of 1:1:1 carbron tetrachloride:acetonitrile:water (18 ml, total) was added ruthenium (III) chloride hydrate (0.010 g, 0.048 mmol) followed by sodium periodate (0.071 g, 0.32 mmol) under argon. The reaction was stirred at room temperature for 1.5 h. A 1:1 mixture of starting material and desired product was observed after 1.5 h. To the reaction was added an additional amount of ruthenium (III) chloride hydrate and sodium periodate (0.010 g and 0.071 g respectively), and stirring continued at room temperature for 20 minutes. The mixture was filtered through a pad of celite and the filtrate was partitioned between ethyl acetate and water. The combined organic extract was washed successively with: water, brine and dried ($MgSO_4$). After removing the solvent under reduced pressure, flash chromatography of the residue (silica gel, 3:7 ethyl acetate:hexane) afforded the title compound as a yellow oil (0.050 g, 50%).

h) 1-(2-Hydroxy-4-methoxybenzoyl)-2-(3,4-methylenedioxybenzoyl)-5-prop-1-yloxybenzene To a solution of 1-(2-benzyloxy-4-methoxybenzoyl)-2-(3,4-methylenedioxybenzoyl)-5-prop-1-yloxybenzene (0.437 g, 0.84 mmol) in a mixture 1:1 ethyl acetate:hexane (20 ml) was added 10% Pd/C (0.040 g) and the mixture was shaken under hydrogen atmosphere at 60 psi for 24 h. The reaction mixture was filtered through a pad of celite and the filtrate dried ($MgSO_4$). After removing the solvent under reduced pressure, flash chromatography of the residue (silica gel, 3:7 ethyl acetate:hexane) afforded the title compound as a pale yellow oil (0.270 g, 72%).

i) (1RS)-1-Hydroxy-1-[(2-hydroxy-4-methoxy)phenyl]-3-(3,4-methylenedioxyphenyl-6-prop-1-yloxy-1H-isoindole A bomb was charged with 1-(2-hydroxy-4-methoxybenzoyl)-2-(3,4-methylenedioxybenzoyl)-5-prop-1-yloxybenzene (0.270 g, 0.608 mmol), cooled to −78° C. (acetone/dry ice bath), and liquid ammonia (15 ml) was added and the vessel was sealed. The reaction was heated at 65° C. reaching a steady pressure of 300 psi for 24 h. The pressure was slowly released after the mixture had cooled to room temperature, and the resulting residue was dissolved in ethyl acetate. After removing the solvent under reduced pressure, flash chromatography of the residue (silica gel, 1:1 ethyl acetate:hexane) afforded the title compound as a yellow oil (0.200 g, 76%).

j) (1RS,3RS)-3-[(2-Hydroxy-4-methoxy)phenyl]-1-(3,4-methylenedioxyphenyl)-5-prop-1-yloxy-isoindoline To a flask containing dry ether (2 ml) was added with stirring aluminum chloride (0.037 g, 0.28 mmol) at 0° C. under argon, followed by 1M lithium aluminum hydride in THF (0.28 ml, 0.28 mmol). The mixture was stirred at 0° C. for 15 minutes, then to it was rapidly added (1RS)-1-Hydroxy-1-[(2-hydroxy-4-methoxy)phenyl]-3-(3,4-methylenedioxyphenyl-6-prop-1-yloxy-1H-isoindole (0.043 g, 0.10 mmol). After stirring for 20 minutes at 0° C. the reaction was quenched with water, 15% sodium hydroxide, and water. The mixture was extracted with ethyl acetate and the combined organic extract was washed successively with: water, brine and dried (MgSO$_4$). After removing the solvent under reduced pressure, flash chromatography of the residue (silica gel, 3:7 ethyl acetate:hexane) afforded the title compound as a pale yellow solid (0.012 g, 28%).

k) Methyl trifluoromethylsulfonyloxyacetate

To a solution of triflic anhydride (3.7 ml, 20.0 mmol) in methylene chloride (10 ml) at −5° C. under argon, was added dropwise over 30 minutes a solution of methyl glycolate (1.8 g, 20.0 mmol), pyridine (1.55 ml, 20.0 mmol), and anhydrous methylene chloride (5 ml). The reaction was allowed to stir at between 0°–5° C. for 1.5 h. The mixture was then washed with water several times. The organic extract was then washed with water, brine, and dried (MgSO$_4$). After removing the solvent under reduced pressure, flash chromatography of the residue (silica gel, methylene chloride) afforded the title compound as a colorless oil (3.0 g, 68%).

l) Methyl(1RS,3RS)-3-[(2-hydroxy-4-methoxy)phenyl]-1-(3,4-methylenedioxyphenyl)-5-prop-1-yloxy-(1H,3H-dihydroisoindol-2yl)acetate To a solution of (1RS,3RS)-3-[(2-hydroxy-4-methoxy)phenyl]-1-(3,4-methylenedioxyphenyl)-5-prop-1-yloxy isoindoline (0.060 g, 0.14 mmol) in methylene chloride (3 ml) was added triethylamine (0.040 ml, 0.28 mmol) followed by methyl trifluoromethlysulfonyloxyacetate (0.065 g, 0.28 mmol) under argon. The reaction was stirred at room temperature for 24 h. The mixture was then partitioned between 1N HCl and ethyl acetate. The organic extract was washed successively with water, brine and dried (MgSO$_4$). After removing the solvent under reduced pressure, flash chromatography of the residue (silica gel, 2:8 ethyl acetate:hexane) afforded the title compound as a colorless oil (0.040 g, 57%).

m) Methyl(1RS,3RS)-3-[(2-carbomethoxymethoxy-4-methoxy)phenyl]-1-(3,4-methylenedioxyphenyl)-5-prop-1-yloxy-(1H,3H-dihydroisoindo-2-yl)acetate To a solution of methyl(1RS,3RS)-3-[(2-hydroxy-4-methoxy)phenyl]-1-(3,4-methylenedioxyphenyl)-5-prop-1-yloxy (1H,3H-dihydroisoindol-2yl)acetate (0.040 g, 0.08 mmol) in dry DMF (0.5 ml) was added potassium carbonate (0.11 g, 0.8 mmol) under argon. The mixture was stirred at room temperature for 20 minutes, then ethyl bromoacetate (0.012 ml, 0.1 mol) added and stirring continued for 24 h. The reaction was quenched with 1N HCl and extracted with ethyl acetate. The combined organic extract was washed successively with water, brine and dried (MgSO$_4$). After removing the solvent under reduced pressure, flash chromatography of the residue (silica gel, 3:7 ethyl acetate:hexane) afforded the title compound as a colorless oil (0.030 g, 64%).

n) (1RS,3RS)-3-[(2-Carboxymethoxy-4-methoxy)phenyl]-1-(3,4-methylenedioxyphenyl)-5-prop-1-yloxy-(1H,3H-dihydroisoindol-2-yl)acetic acid To a solution of Methyl(1RS,3RS)-3-[(2-carbomethoxymethoxy-4-methoxy)phenyl]-1-(3,4-methylenedioxyphenyl)-5-prop-1-yloxy-(1H,3H-dihydroisoindol-2-yl)acetate (0.030 g, 0.052 mmol) in warm isopropanol (2 ml) was added 6N sodium hydroxide (0.043 ml, 0.26 mmol). The reaction was stirred at reflux for 2 h. The mixture was then quenched with 3N HCl and extracted with ethyl acetate. The combined organic extract was washed successively with water, brine and dried (MgSO$_4$). After removing the solvent under reduced pressure, purification of the resulting residue by reversed phase HPLC (1:1 acetonitrile:water, and 1% TFA) afforded the title compound as a white solid (0.020 g, 71%). MS (ESI) m/e 536 [M+H]$^+$; mp: 154°–158 ° C. (dec.); Anal. (C$_{31}$H$_{30}$F$_3$NO$_{11}$.3.5H$_2$O) calcd. C, 41.95; H, 3.73; N, 1.66: found: C, 42.14; H, 3.82; N, 1.33.

EXAMPLE 2

Preparation of (1RS,3RS)-3-(4-Methoxyphenyl)-1-(3,4-methylenedioxyphenyl)-(1H,3H-dihydroisoindol-2yl)acetic acid a) 2-Hydroxy-4'-methoxyacetophenone To a mixture of aluminum chloride (22.5 g, 0.169 mol) and chlorobenzene (50 ml) was added anisole (18 g, 0.166 mol) at 10° C. Keeping the temperature below 25° C., o-methoxybenzoyl chloride (28 g, 0.164 mol) was added dropwise to the reaction. The solution was stirred for 30 minutes at room temperature, then it was heated on a steam bath for 2 h. After cooling to 0°–5° C. in an ice bath the mixture was treated with 10% HCl (100 ml) and stirred at room temperature for 18 h. The product was extracted with ether (3×100 ml) and the combined organic extract was washed with 5% sodium hydroxide (3×50 ml). The combined aqueous extract was acidified with concentrated HCl and extracted with ether (3x). The combined organic extract was washed with water and dried (MgSO$_4$). Removal of the solvent under reduced pressure gave the title compound as an amber oil (22.9 g, 61%).

b) 2-Hydroxy-4'-methoxyacetophenone 3,4-methylenedioxybenzoylhydrazone

To a solution of 3,4-methylenedioxybenzhydrazine (4.89 g, 27.1 mmol), 2-Hydroxy-4'-methoxyacetophenone (6.19 g, 27.1 mmol) in isopropanol (150 ml) was added sodium acetate (1 g), and the mixture was stirred at reflux for 24 h, after which only a small amount of product had formed. An additional amount of sodium acetate (1 g) was added to the reaction and stirring at reflux continued for 24 h during which time a precipitate formed. The precipitate was filtered while hot to afford the title compound as a solid (3.8 g, 36%).

c) 1-(4-Methoxybenzoyl)-2-(3,4-methylenedioxybenzoyl)benzene

To a solution of 2-Hydroxy-4'-methoxyacetophenone 3,4-methylenedioxybenzoylhydrazone (3.83 g, 9.82 mmol) of in acetic acid (40 ml) was added iodobenzene diacetate (6.32 g, 19.6 mmol) and the suspension was stirred at room temperature for 24 h and then stirred at reflux for 3 h. The mixture was cooled, then partitioned between ethyl acetate and water. The combined organic extract was washed successively with: water, brine and dried (MgSO$_4$). After removing the solvent under reduced pressure, flash chromatography of the residue (silica gel, 3:7 ethyl acetate:hexane) afforded the title compound as an off white solid (2.4 g, 68%).

d) (1RS)-1-Hydroxy-1-(4-methoxyphenyl)-3-(3,4-methylenedioxyphenyl)-1H-isoindole A bomb was charged 1-(4-methoxybenzoyl)-2-(3,4-methylenedioxybenzoyl)benzene (1.0 g, 2.8 mmol) was cooled to −78° C. (acetone/dry ice bath), and liquid ammonia (20 ml) was added and the vessel was sealed. The reaction was heated at 70° C. reaching a steady pressure of 300 psi for 24 h. The pressure was slowly released after the mixture had cooled to room temperature, and the brown residue was partitioned between ethyl acetate and water. The organic extract was acidified with 3N HCl. The resulting aqueous layer (containing the hydrochloride salt) was washed with ethyl acetate, then basified by treatment with concentrated ammonium hydroxide and extracted with ethyl acetate. The combined organic extract was successively washed with water brine and dried ($MgSO_4$). Removal of the solvent under reduced pressure gave an isomeric mixture of the title compound as a brown foam (0.900 g, 90%).

e) (1RS,3RS)-3-(4-Methoxyphenyl)-1-(3,4-methylenedioxyphenyl)isoindoline

To a flask containing dry ether (2 ml) was added with stirring aluminum chloride (0.037 g, 0.28 mmol) at 0° C. under argon, followed by 1M lithium aluminum hydride in THF (0.28 ml, 0.28 mmol). The mixture was stirred at 0° C. for 5 minutes, then to it was rapidly added (1RS)-1-Hydroxy-1-(4-methoxyphenyl)-3-(3,4-methylenedioxyphenyl)-1H-isoindole (0.050 g, 0.14 mmol), followed by dry THF (2 ml). After stirring for 10 minutes at 0° C. the reaction was quenched with water, 15% sodium hydroxide, and water. The mixture was extracted with ethyl acetate and the combined organic extract was successively washed with: water, brine and dried ($MgSO_4$). After removing the solvent, flash chromatography of the residue (silica gel, 3:7 ethyl acetate:hexane) afforded the title compound as a yellow solid (0.030 g, 45%). MS (ESI) m/e 346 [M+H]$^+$; mp: 123°–125° C.

f) Methyl(1RS,3RS)-3-(4-methoxyphenyl)-1-(3,4-methylenedioxyphenyl)-(1H,3H-dihydroisoindol-2yl)acetate To a solution of (1RS,3RS)-1-(4-methoxyphenyl)-3-(3,4-methylenedioxyphenyl)isoindoline (0.140 g, 0.41 mmol) in methylene chloride (3 ml) was added triethylamine (0.085 ml, 0.61 mmol) followed by methyl trifluoromethlysulfonyloxyacetate (0.065 g, 0.28 mmol) under argon. The reaction was stirred at room temperature for 2.5 h. The mixture was then partitioned between ethyl acetate and water. The combined organic extract was washed successively with: water, brine and dried ($MgSO_4$). After removing the solvent under reduced pressure, flash chromatography of the residue (silica gel, 3:7 ethyl acetate:hexane) afforded the title compound as a oil (0.130 g, 76%).

g) (1RS,3RS)-3-(4-Methoxyphenyl)-1-(3,4-methylenedioxyphenyl)-(1H,3H-dihydroisoindol-2yl) acetic acid To a solution of Methyl(1RS,3RS)-3-(4-methoxyphenyl)-1-(3,4-methylenedioxyphenyl)-(1H,3H-dihydroisoindol-2yl)acetate (0.130 g, 0.31 mmol) in isopropanol (3 ml) was added 6M sodium hydroxide (0.151 mmol). The reaction was stirred at reflux for 24 h. The organic solvent was removed and the aqueous layer was acidified with 3N HCl and extracted with ethyl acetate. The organic extract was washed successively with: water, brine and dried ($MgSO_4$). Removal of the solvent under reduced pressure gave the title compound as a colorless oil (0.100 g, 81%). MS (ESI) m/e 404 [M+H]$^+$; Anal. ($C_{24}H_{21}NO_5$.) calcd. C, 71.45; H, 5.25; N, 3.47: found: C, 71.44; H, 5.17; N, 3.42; $^1$H NMR (400 MHz, $CDCl_3$) δ7.35 (d, J=8.7 Hz, 2H), 7.17 (d, J=8.7 Hz, 2H), 6.95–6.80 (mm, 7H), 5.94 (s, 2H), 5.34 (s, 2H), 3.81 (s, 3H), 3.47 (s, 2H).

EXAMPLE 3

Formulations for pharmaceutical use incorporating compounds of the present invention can be prepared in various forms and with numerous excipients. Examples of such formulations are given below.

Inhalant Formulation

A compound of formula I (1 mg to 100 mg) is aerosolized from a metered dose inhaler to deliver the desired amount of drug per use.

| Tablets/Ingredients | Per Tablet |
| --- | --- |
| 1. Active ingredient (Cpd of Formula I) | 40 mg |
| 2. Corn Starch | 20 mg |
| 3. Alginic acid | 20 mg |
| Sodium alginate | 20 mg |
| 5. Mg stearate | 1.3 mg |
| | 2.3 mg |

Procedure for Tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its converion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

We claim:

1. A compound of Formula (I):

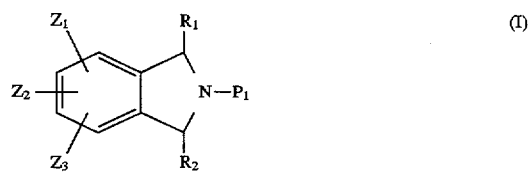

wherein:

$R_1$ is —X($CH_2$)$_n$Ar $R_2$ is hydrogen, Ar or $C_{1-4}$alkyl;

$P_1$ is tetrazole, $SO_2NR_7R_{11}$, $CONR_7SO_2R_{11}$, or ($CH_2$)$_s R_8$;

$R_3$ and $R_5$ are independently hydrogen, $R_{11}$, OH, $C_{1-8}$alkoxy, $S(O)_q R_{11}$, $N(R_6)_2$, Br, F, I, Cl, $CF_3$, $NHCOR_6$, $R_{11}CO_2R_7$, —X—$R_9$—Y, or —X(CH$_2$)$_n R_8$ wherein each methylene group within —X(CH$_2$)$_n R_8$ may be unsubstituted or substituted by one or two —(CH$_2$)$_n$Ar groups;

$R_4$ is hydrogen, $R_{11}$, OH, $C_{1-5}$alkoxy, $S(O)_q R_{11}$, $N(R_6)_2$, —X(R$_{11}$), Br, F, I, Cl or $NHCOR_6$ wherein the $C_{1-5}$alkoxy may be unsubstituted or substituted by OH, methoxy or halogen;

$R_6$ is independently hydrogen or $C_{1-4}$alkyl;

$R_7$ is independently hydrogen, $C_{1-10}$alkyl, $C_{2-10}$alkenyl or $C_{2-8}$ alkynyl, all of which may be unsubstituted or substituted by one or more OH, $N(R_6)_2$, $CO_2R_{12}$, halogen or $XC_{1-5}$alkyl; or $R_7$ is (CH$_2$)$_n$Ar;

$R_8$ is hydrogen, $R_{11}$, $CO_2R_7$, $CO_2C(R_{11})_2O(CO)XR_7$, $PO_3(R_7)_2$, $SO_2NR_7R_{11}$, $NR_7SO_2R_{11}$ $CONR_7SO_2R_{11}$, $SO_3R_7$, $SO_2R_7$, $P(O)(OR_7)R_7$, CN, —CO$_2$(CH$_2$)$_m$C(O)N(R$_6$)$_2$, C(R$_{11}$)$_2$N(R$_7$)$_2$, C(O)N(R$_6$)$_2$ or tetrazole;

$R_9$ is (CH$_2$)$_n$, $C_{1-10}$alkylene, $C_{2-10}$alkenylene or phenylenyl, all of which may be unsubstituted or substituted by one or more OH, $N(R_6)_2$, COOH, halogen, or $R_9$ is C=O or $XC_{1-5}$alkyl;

$R_{11}$ is hydrogen, Ar, $C_{1-8}$alkylene, $C_{2-8}$alkenylene, $C_{2-8}$alkynylene, all of which may be unsubstituted or substituted by one or more OH, $CH_2OH$, $N(R_6)_2$ or halogen;

$R_{12}$ is hydrogen, $C_{1-6}$alkyl, $C_{2-6}$alkenyl or $C_{2-7}$alkynyl;

X is (CH$_2$)$_n$, O or $NR_6$;

Y is $CH_3$ or X(CH$_2$)$_n$Ar;

Ar is:

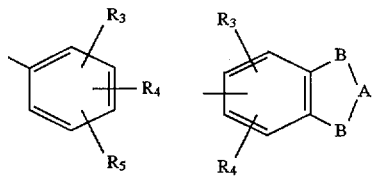

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is C=O, or [C(R$_6$)$_2$]$_m$;

B is —CH$_2$— or —O—;

$Z_1$ and $Z_2$ are independently hydrogen, $C_{1-8}$alkyl, $C_{2-8}$alkenyl, $C_{2-8}$alkynyl, OH, $C_{1-8}$alkoxy, $S(O)_q C_{1-5}$alkyl, $N(R_6)_2$, Br, F, I, C$_1$, $NHCOR_6$, —X—$R_9$-Y, —X(CH$_2$)$_n R_8$, phenyl, benzyl or $C_{3-6}$cycloalkyl wherein the $C_{1-8}$alkyl, $C_{2-8}$alkenyl or $C_{2-8}$alkynyl may be optionally substituted by COOH, OH, CO(CH$_2$)$_n$CH$_3$, CO(CH$_2$)$_n$CH$_2$N(R$_6$)$_2$, or halogen; or $Z_1$ and $Z_2$ together may be —O—A—O— on contiguous carbons;

$Z_3$ is $Z_1$ or —X—$R_9$—Y;

q is zero, one or two;

n is an integer from 0 to six;

s is an integer from one to six;

m is 1, 2 or 3; and the dotted line indicates the optional presence of a double bond; provided P$_1$ is not (CH$_2$)$_s$NH$_2$; and further provided Z$^1$ and Z$^2$ and Z$^3$ are not all hydrogen; or a pharmaceutically acceptable salt thereof.

2. A pharmaceutical composition comprising a compound of claim 1 and a pharmaceutically acceptable carrier.

3. A method of antagonizing endothelin receptors which comprises administering to a subject in need thereof, an effective amount to antagonize endothelin receptors of a compound of claim 1.

4. A method of treating hypertension which comprises administering to a subject in need thereof an effective amount of a compound of claim 1.

5. A method of treating renal failure which comprises administering to a subject in need thereof, an effective amount of a compound of claim 1.

6. A method of treating cerebrovascular disease which comprises administering to a subject in need thereof, an effective amount of a compound of claim 1.

* * * * *